United States Patent [19]
Bal-Tembe et al.

[11] Patent Number: 6,107,335
[45] Date of Patent: Aug. 22, 2000

[54] ESCULENTIN A AND ESCULENTIN B, A PROCESS FOR THEIR PREPARATION, AND THEIR USE IN THE MANUFACTURE OF MEDICAMENTS

[75] Inventors: Swati Bal-Tembe, Mumbai; Erra Koteswara Satya Vijaya Kumar, Bombay; Vijay Bhagwan Deore, Maharashtra; Kalpana Sanjay Joshi, Thane, all of India

[73] Assignee: Hoechst Marion Roussel Deutschland GmbH, Frankfurt am Main, Germany

[21] Appl. No.: 09/192,501

[22] Filed: Nov. 17, 1998

[30] Foreign Application Priority Data

Nov. 18, 1997 [EP] European Pat. Off. .............. 97120143

[51] Int. Cl.$^7$ .......................... A61K 31/34; C07D 307/77
[52] U.S. Cl. ............................. 514/468; 549/458
[58] Field of Search .............................. 549/458; 514/468

[56] References Cited

U.S. PATENT DOCUMENTS 5,468,772  11/1995  Xu et al. ................................. 514/453

OTHER PUBLICATIONS

Morita H. et al., "Structures and Cytotoxic Activity Relationship of Casearins, New Clerodane Diterpenes from *Casearia sylvestris* Sw.," *Chem. Pharm. Bull.*, vol. 39, No. 3, pp. 693–697 (Mar. 1991).

Itokawa H. et al., "New Antitumor Principles, Casearins A–F, for *Casearia sylvestris* Sw. (Flacourtiaceae)," *Chem. Pharm. Bull.*, vol. 38, No. 12, pp. 3384–3388 (Dec. 1990).

K. D. Choudhury et al., "Phytochemical and Hypoglycemic Investigation of *Casearia Esculenta*," *Journal of Pharmaceutical Sciences*, vol. 56, No. 11, pp. 1405–1409, Nov. 1967.

J. D. Hooker, "Sabiaceæ to Cornaceæ," *Flora of British India*, vol. II, pp. 590–598, L. Reeve & Co., London, 1879.

*Primary Examiner*—Ba K. Trinh
*Attorney, Agent, or Firm*—Finnegan, Henderson, Farabow, Garrett & Dunner, L.L.P.

[57] ABSTRACT

The compounds 18β, 19β-diacetyloxy-18α, 19α-epoxy-3, 13(16), 14-clerodatrien-2-one (Esculentin A) and 18β, 19β-diacetyloxy-18α, 19α-epoxy-3, 12, 14-clerodatrien-2β-isovaleryloxy-6β, 7α-diol (Esculentin B) obtained from plants belonging to the Samydaceae family, particularly *Casearia esculenta*, a process for their preparation, and their use in the manufacture of medicaments. The compounds are particularly useful as anti-inflammatory and/or anti-cancer agents.

19 Claims, 6 Drawing Sheets

ESCULENTIN A AND ESCULENTIN B, A PROCESS FOR THEIR PREPARATION, AND THEIR USE IN THE MANUFACTURE OF MEDICAMENTS

The present invention relates to the compounds 18β, 19β-diaetyloxy-18α, 19α-epoxy-3, 13(16), 14-clerodatrien-2-one (Esculentin A) and 18β, 19β-diacetyloxy-18α, 19α-epoxy-3, 12, 14-clerodatrien-2β-isovaleryloxy-6β, 7α-(diol (Esculentin B) obtained from plants belonging to the Samydaceae family, particularly *Casearia esculenta*, a process for their preparation, and their use in the the manufacture of medicaments.

Rheumatoid arthritis is a chronic inflammatory degenerative disease affecting about 1% of the population. Drug therapy with disease modifying agents such as methotrexate, sulfasalazine, gold salts or cyclosporin has been shown to reduce joint destruction and slow the disease. However, all the current disease modifying drugs have side-effects and none is capable of stopping the disease completely or slowing it down sufficiently when it is very aggressive. Cytokines such as IL-1 and TNF-α are key mediators in the inflammatory process and have been detected in the synovial fluid of rheumatoid arthritic patients. Compounds which inhibit the formation or release of cytokines may play a key role in interrupting the disease progression and ultimately lead to long term remission of rheumatoid arthritis.

Esculentins A and B may be described as cytokine inhibitors. They belong to diterpene class and are represented by the formulae 1 and 2 below:

Esculentin A (1)

Esculentin B (2)

Esculentin A and Esculentin B may be chemically described as 18β,19β-diacetyloxy-18α,19α-epoxy-3,13 (16),14-clerodatrien-2-one and 8β,19β-diacetyloxy-18α, 19α-epoxy-3,12,14-clerodatrien-2β-isovaleryloxy-6β,7α-diol, respectively. The relative stereochemistries of compounds of formulae 1 and 2 were established on the basis of coupling constants and Nuclear Overhauser Effect (NOE) studies. A chemical abstract literature search using search keys of the molecular formulae established that both the compounds of formulae 1 and 2 are new.

The Samydaceae family consists of about 150 plant species distributed over 3 genera. Among these, some of the Casearia species and *Hornalium zeylanicum* are found to be growing in India. The morphological details and distribution of the plant species of these genera are described in literature (J. H. Hooker "Flora of British India," Vol. II, p. 590–598).

According to one aspect of the invention there are provided compounds of the formula 1 or 2 above and their pharmaceutically acceptable derivatives.

We have found that the compounds of the formulae 1 and 2 can be solvent extracted from plants belonging to the Samydaceae family, particularly *Casearia esculenta*. Accordingly, an object of the invention is to provide a process for the isolation of the new compounds of the formulae 1 and 2 from plants belonging to the Samydaceae family, particularly *Casearia esculenta*.

According to a second aspect of the invention, therefore, there is provided a process for the preparation of new pharmacologically active 18β, 19β-diacetyloxy-18α, 19α-epoxy-3, 13(16), 14-clerodatrien-2-one (Esculentin A) and/or 18β, 19β-diacetyloxy-18α, 19α-epoxy-3, 12, 14-clerodatrien-2β-isovaleryloxy-6β, 7α-diol (Esculentin B) of the formulae 1 and 2, respectively, from plants belonging to the Samydaceae family particularly *Casearia esculenta*, and of their pharmaceutically acceptable derivatives, comprising extracting the plant material with an organic solvent in the ratio 1:2 to 10 parts by weight of the plant material to the organic solvent at a pH 5–8 and recovering the compounds of the formula 1 and/or 2 from the solvent extract and, optionally, converting the compounds of the formulae 1 and/or 2 into pharmaceutically acceptable derivatives thereof.

Further aspects of the invention include: pharmaceutical compositions containing a compound of the formula 1 and/or 2 together with a pharmacologically tolerated auxiliary and/or excipient and the use of compounds of the formula 1 or 2 for the manufacture of a medicament for the treatment of chronic inflammation or cancer.

Additional features and advantages of the invention are set forth in the description that follows, and in part will be apparent from the description or may be learned from the practice of the invention. Both the foregoing general description and the following detailed description of the invention are exemplary and explanatory only and are not restrictive of the claimed invention.

BRIEF DESCRIPTION OF THE DRAWINGS

The accompanying drawings, which are incorporated in and constitute a part of this specification, illustrate preferred embodiments of the invention and together with the description, serve to explain the principles of the invention. In the drawings.

The plant material includes different parts of the plant namely, leaves, twigs, stem bark, stem wood, root bark and root wood, preferably twigs. The twigs of *Casearia esculenta* were collected around Mumbai, India. A voucher specimen of the species is preserved at the Herbarium of the Research Centre, Hoechst Marion Roussel Limited, Mulund (W), Mumbai-400 080, India.

The organic solvent used in the process is, for example, petroleum ether (hexane), ethyl acetate, dichloromethane, chloroform or a lower alcohol such as methanol, ethanol, isopropanol or butanol. The extraction is preferably carried out with petroleum ether followed by dichloromethane. Extraction is preferably carried out in the ratio of 1:5 parts by weight of the plant material to the organic solvent. Extraction is preferably carried out at a pH 7.

The active substances Esculentin A and Esculentin B of the invention may, for example, be recovered from the extract as follows:

By fractionation using any of the following techniques: normal phase chromatography (using alumina or silica gel as stationary phase and eluents such as petroleum ether, ethyl acetate, chloroform, methanol or combinations thereof), reverse phase chromatography (using reverse phase silica gel like dimethyloctadecylsilylsilica gel, also called RP-18; or dimethyloctylsilylsilica gel, also called RP-8; as stationary phase and eluents such as water, buffers viz. phosphate, acetate, citrate (pH 2–8) and organic solvents such as methanol, acetonitrile or acetone, or combinations of these solvents), gel permeation chromatography using resins such as SEPHADEX LH-20 (Pharmacia Chemical Industries, Sweden), TSK GEL and TOYOPEARL HW (TosoHaas, Tosoh Corporation, Japan) in solvents such as methanol, chloroform or ethyl acetate or their combinations or SEPHADEX G-10 and G-25 in water; or by counter-current chromatography using a biphasic eluent system made up of two or more solvents such as water and chloroform. In the above fractionation techniques, the SEPHADEX resins are cross-linked dextran gels; the TSK GEL and TOYOPEARL HW resins are rigid, hydrophilic matrices prepared from a copolymer of ethylene glycol and methacrylate polymers. These techniques may be used repeatedly or a combination of the different techniques may be used. The preferred method is chromatography over reverse phase modified silica gel (RP-18) followed by silica gel.

Esculentins A and B may be administered orally, intramuscularly or intravenously. Pharmaceuticals which contain Esculentins A and B as the active substances are also a subject of the invention. They may be prepared by mixing the new compounds with one or more pharmacologically tolerated auxiliaries and/or excipients such as, for example, fillers, emulsifiers, lubricants, masking flavors, colorants or buffer substances, and converted into a suitable pharmaceutical form such as, for example, tablets, coated tablets, capsules or a suspension or solution for parenteral administration.

Examples of auxiliaries and/or excipients which may be mentioned are tragacanth, lactose, talc, agar-agar, polyglycols, ethanol and water. Suitable and preferred for parenteral administration are suspensions or solutions in water. It is also possible to administer the active substances as such, without vehicles or diluents, in a suitable form, for example, in capsules.

The compounds of the formulae 1 and 2 may be converted into their pharmaceutically acceptable derivatives like esters and ethers. Esters may be prepared by reacting the compound of formula 2 with carboxylic acids in the presence of a catalyst or by treating the compound of formula 2 with acylating agents such as acid chlorides. Other methods of preparation of esters are given in literature (Advanced Organic Synthesis, 4th Edition, J. March, John Wiley & Sons, 1992).

Ethers may be prepared from the compound of formula 2 by reaction with alkylating agents under basic conditions. Other methods of preparation of ethers are given (Advanced Organic Synthesis, 4th Edition, J. March, John Wiley & Sons, 1992).

The compound of formula 1 may be reduced to the corresponding alcohol using various reducing agents described in literature (Advanced Organic Synthesis, 4th Edition, J. March, John Wiley & Sons, 1992) and the alcohol may, further, be converted to esters and ethers as described earlier for the compound of formula 2.

The present invention is further illustrated by the following example which is designed to teach those of ordinary skill in the art how to practice the invention. The following example is illustrative of the invention but should not be construed as limiting the scope of the invention as claimed.

EXAMPLE 1

Dried and ground twigs of *Casearia esculenta* were extracted successively with petroleum ether and dichloromethane, in a ratio of 1 kg twigs: 6.5 liters of solvent. The combined dichloromethane extracts were concentrated under reduced pressure of 10–100 mm of Hg at 35° C. to get crude material (200 g) which showed anti-arthritic activity at a dose of 20 mg/kg administered daily for 12 days in the Perper's model of adjuvant arthritis (Ref: The use of a standardized adjuvant arthritis assay to differentiate between anti-inflammatory and immunosuppressive agents. R J Perper, B. Alvarez, C. Colombo and H. Schroder. Proc. Soc. Exp. Biol. Med., 137, 506 (1971)). 18 g of the crude material was loaded in three separate lots of 6 g each on a column (Height: 7 cm; Diameter: 10.5 cm) of reverse phase silica gel (RP-18) (275 g). The column was successively eluted under vacuum with 500 ml of 50% methanol in water and 1 liter each of 60%, 80% and 90% methanol in water and finally with methanol. The flow rate was maintained at 15 ml/min. The fractions were collected in 250 ml size. The active fractions, which eluted out in 80% methanol in water, were combined, concentrated under reduced pressure of 10–100 mm of Hg at 35° C. and lyophilized to obtain 8 g of enriched material.

6 g of the above enriched material was further fractionated on a glass column (Height: 25 cm; Diameter: 6 cm) packed with silica gel (200–300 mesh) to separate the two active substances of the formulae 1 and 2. The column was eluted under a pressure of 0.15 kg/cm$^3$ with 1.5 liter each of 20%, 25%, 30%, 35%, 40%, 45%, 50% and 75% ethylacetate in petroleum ether and finally with ethyl acetate. The flow rate was maintained at 7–8 ml/min and the fractions were collected in 250 ml size. Compound of the formula 1 eluted out in 30% ethyl acetate in petroleum ether, while compound of the formula 2 in 45% ethyl acetate in petroleum ether. The fractions containing compounds of formulae 1 and 2 were pooled separately, concentrated under reduced pressure of 10–100 mm of Hg at 35° C. to dryness to obtain semi-pure compounds of formulae 1 (1.05 g) and 2 (0.745 g).

The compound of formula 1 (1.05 g) was further purified by a silica gel column (4×25 cm) using a step gradient of ethyl acetate in chloroform. Thus, the column was eluted under pressure of 0.15 kg/cm$^3$ with chloroform (500 ml), 1% ethyl acetate in chloroform (250 ml), 1.5% ethyl acetate in chloroform (250 ml), 2% ethyl acetate in chloroform (500 ml), 3% ethyl acetate in chloroform (250 ml), 4% ethyl acetate in chloroform (500 ml) and 5% ethyl acetate in chloroform (500 ml). The flow rate was maintained at 5–6 ml/min. The fractions were collected in 50 ml size. The fractions containing the compound of formula 1, which eluted in 2–4% ethyl acetate, were combined, concentrated under reduced pressure of 10–100 mm of Hg at 35° C. to dryness to get 340 mg of compound of formula 1. This was finally purified in batches by CHROMATOTRON, a preparative, centrifugally accelerated, radial, thin-layer chromatograph (Harrison Research, Palo Alto, Calif.), on a 1 mm thickness silica gel coated plate using 16% ethyl acetate in petroleum ether for elution at a flow rate of 3 ml/min to get pure compound of formula 1 (0.12 g).

The compound of formula 2 (0.6 g) was further purified by medium pressure liquid chromatography (MPLC) on a silica gel column (Height: 25.5 cm; Diameter: 3.7 cm) using 3% methanol in chloroform for elution. The flow rate was maintained at 25 ml/min. The fractions were collected in 50 ml size. The fractions containing compound of formula 2 were combined, concentrated under reduced pressure of 10–100 mm of Hg at 35° C. to dryness to get 0.39 g of semi-pure compound of formula 2, which was finally purified by CHROMATOTRON on a 1 mm thickness silica gel coated plate using 3% methanol in chloroform for elution at a flow rate of 3 ml/min to get a pure compound of formula 2 (0.12 g).

The purity of the compounds of formulae 1 and 2 was checked by HPLC (High Pressure Liquid Chromatography) on a EUROSPHERE 100-C18 (4 mm×250 mm) column using a gradient of 50% acetonitrile in water to 100% in 25 min at a flow rate of 1 ml/min and UV detection at 220 nm. The EUROSPHERE column contains a spherical pebble-gel with a 100 Å pore size, endcapped, with a C-proportion of approximately 14.5%.

The physico-chemical properties of Esculentins A and B of formulae 1 and 2 are summarized in the following Table 1.

TABLE 1

Figure 1:
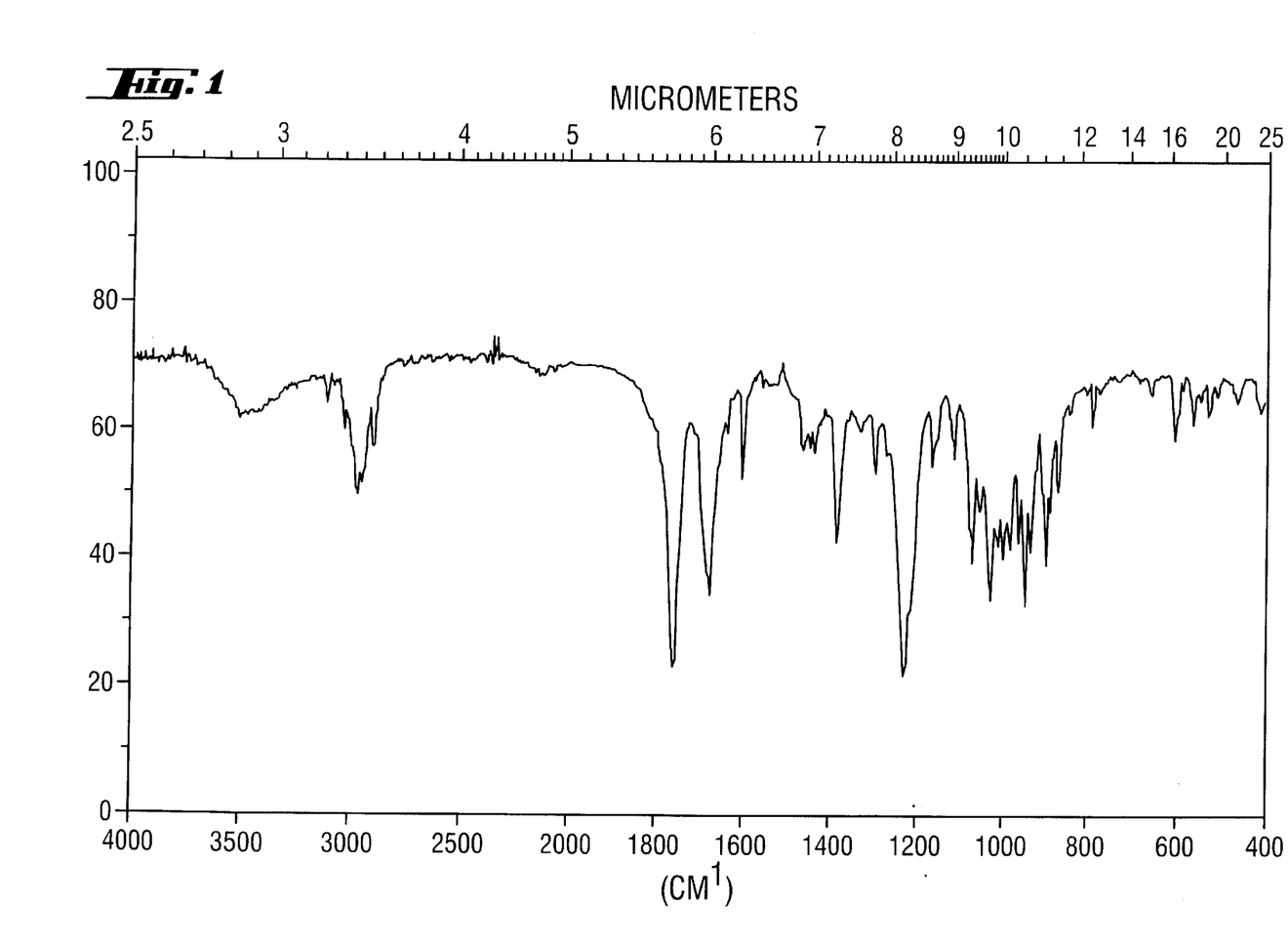
FIG. 1 illustrates the IR (KBr) of Esculentin A.
Figure 2:
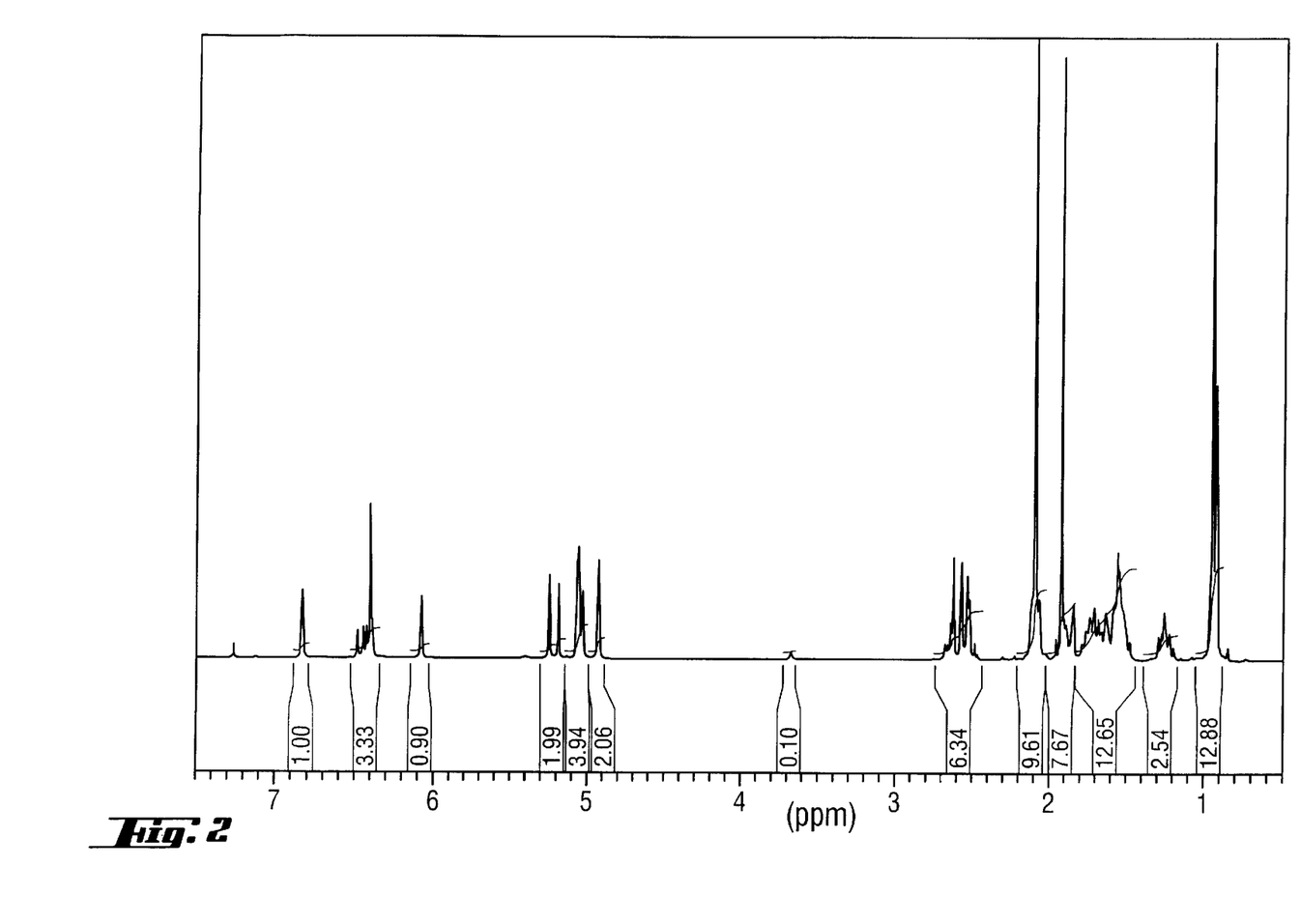
FIG. 2 illustrates the $^1$H NMR (300 MHz, CDCl$_3$) of Esculentin A.
Figure 3:
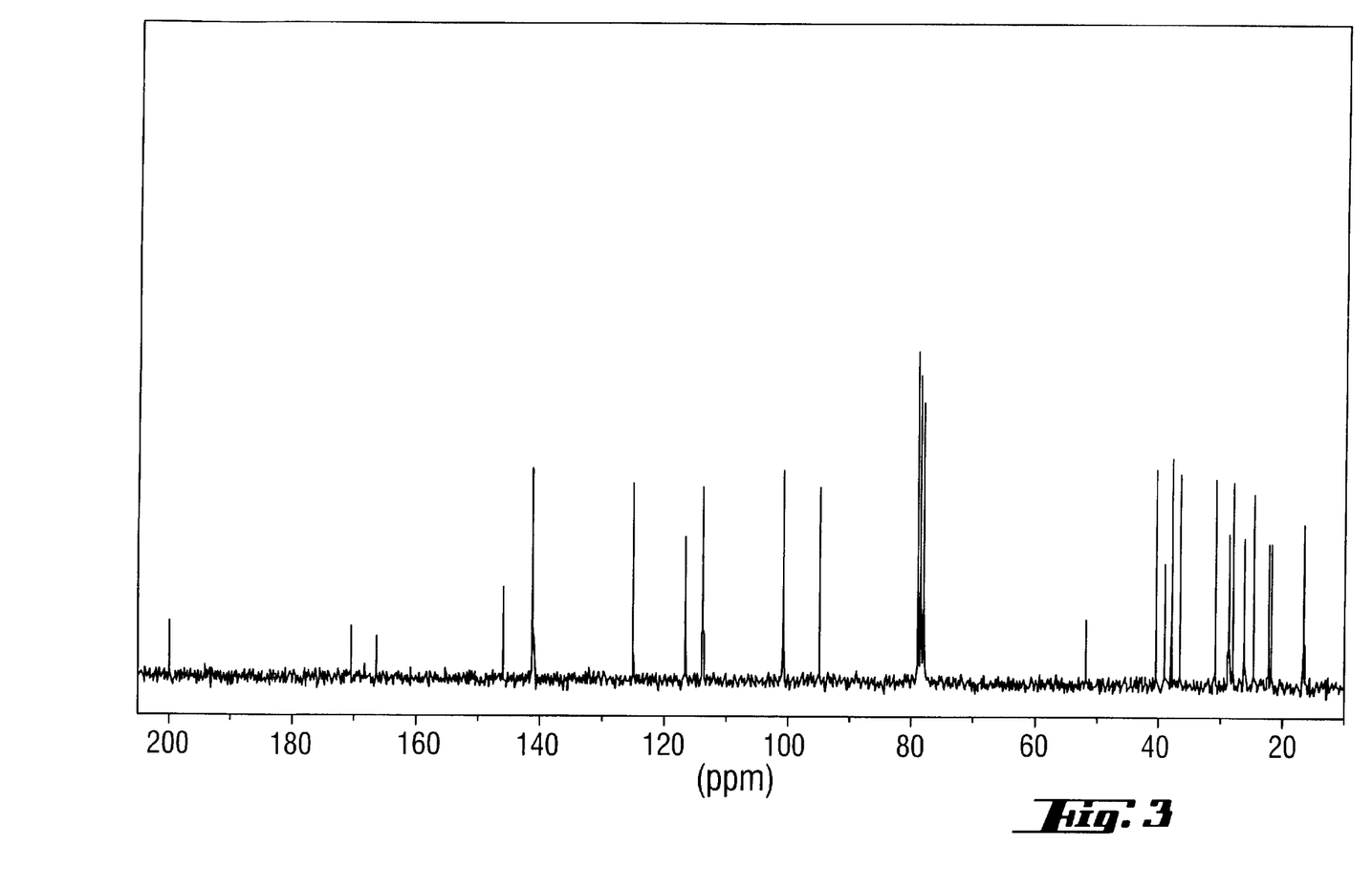
FIG. 3 illustrates the $^{13}$C NMR (75 MHz,CDCl$_3$) of Esculeutin A.
Figure 4:
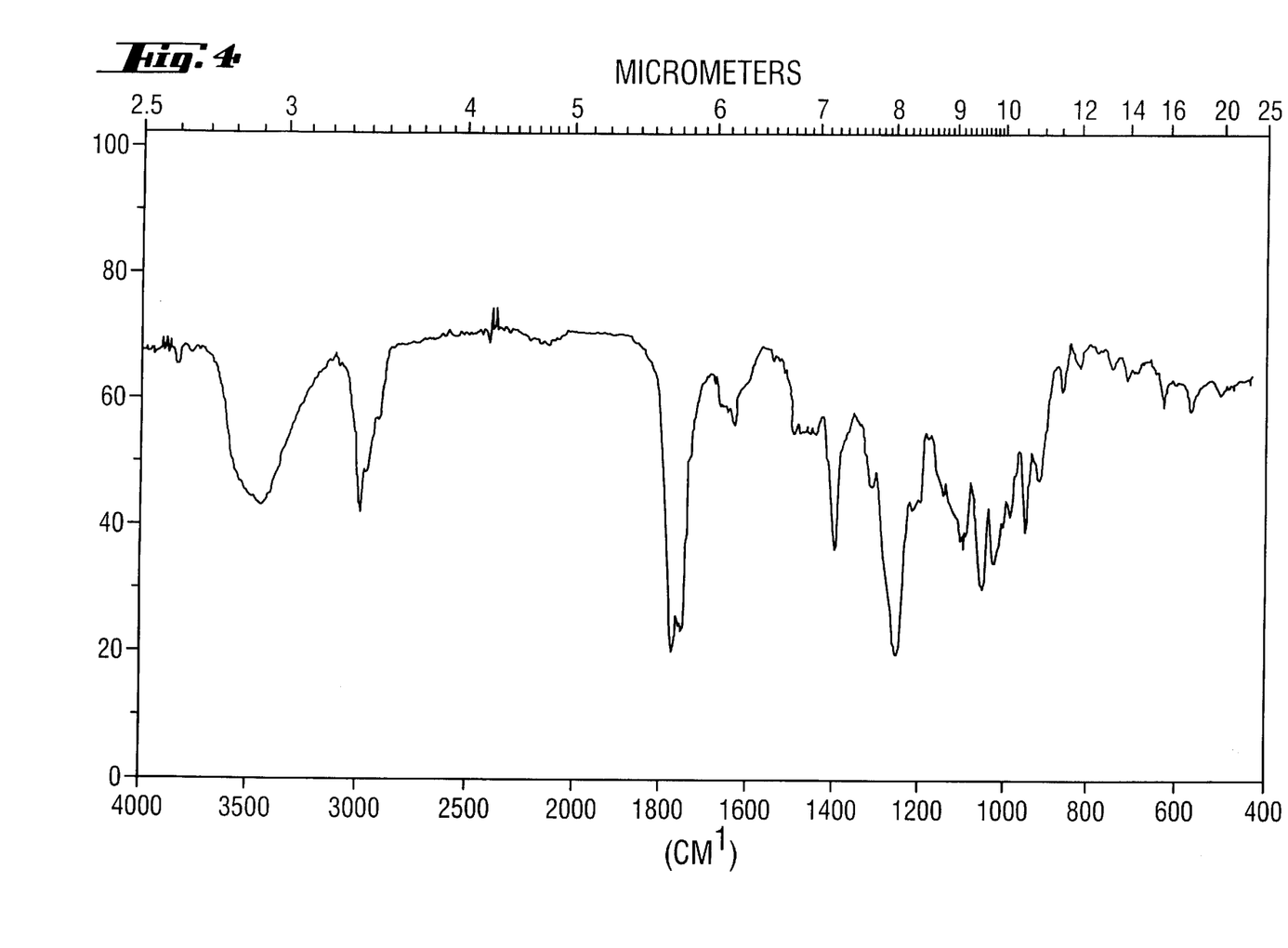
FIG. 4 illustrates the IR (KBr) of Esculentin B.
Figure 5:
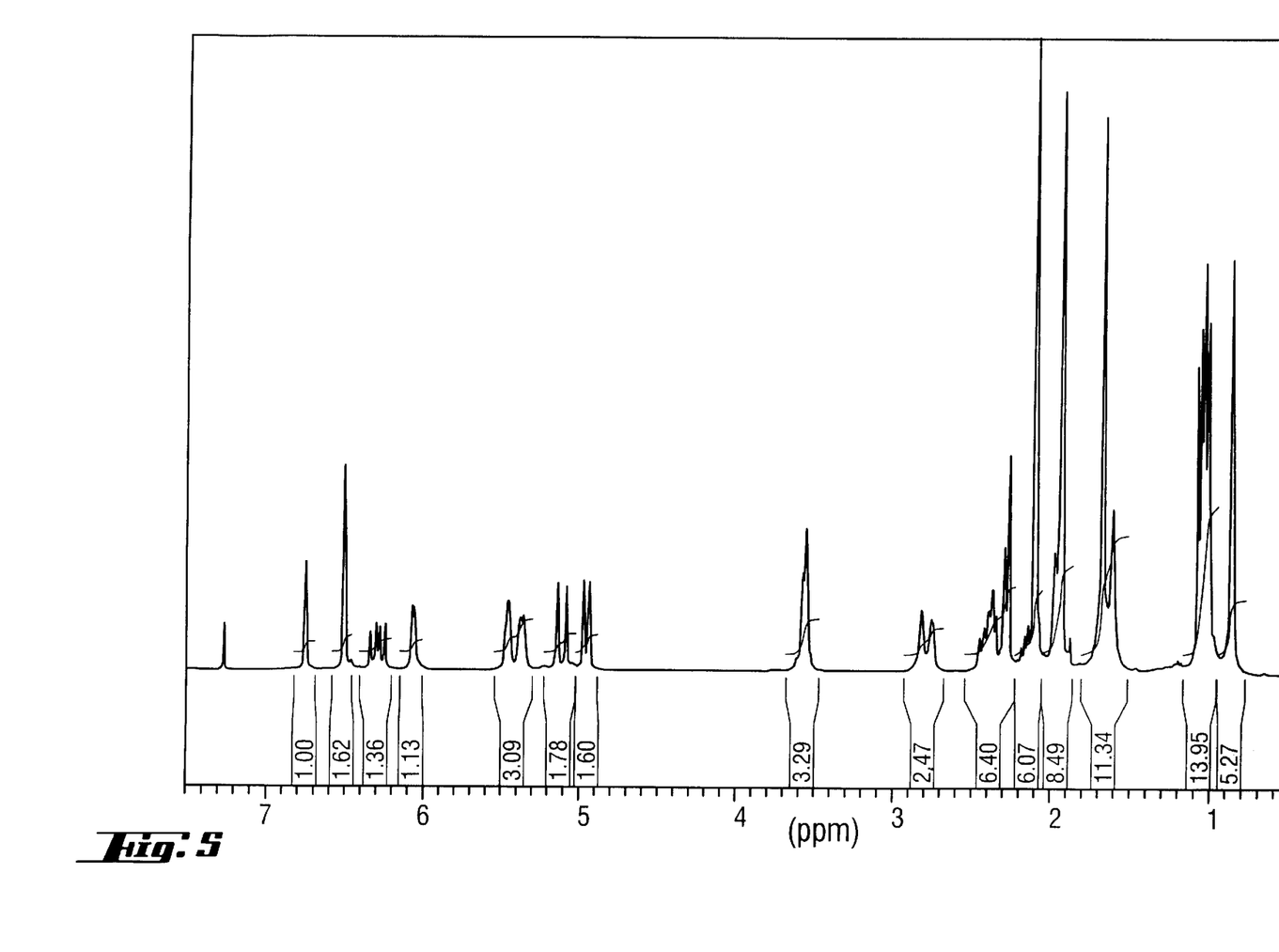
FIG. 5 illustrates the $^1$H NMR (300 MHz,CDCl$_3$) of Esculentin B.
Figure 6:
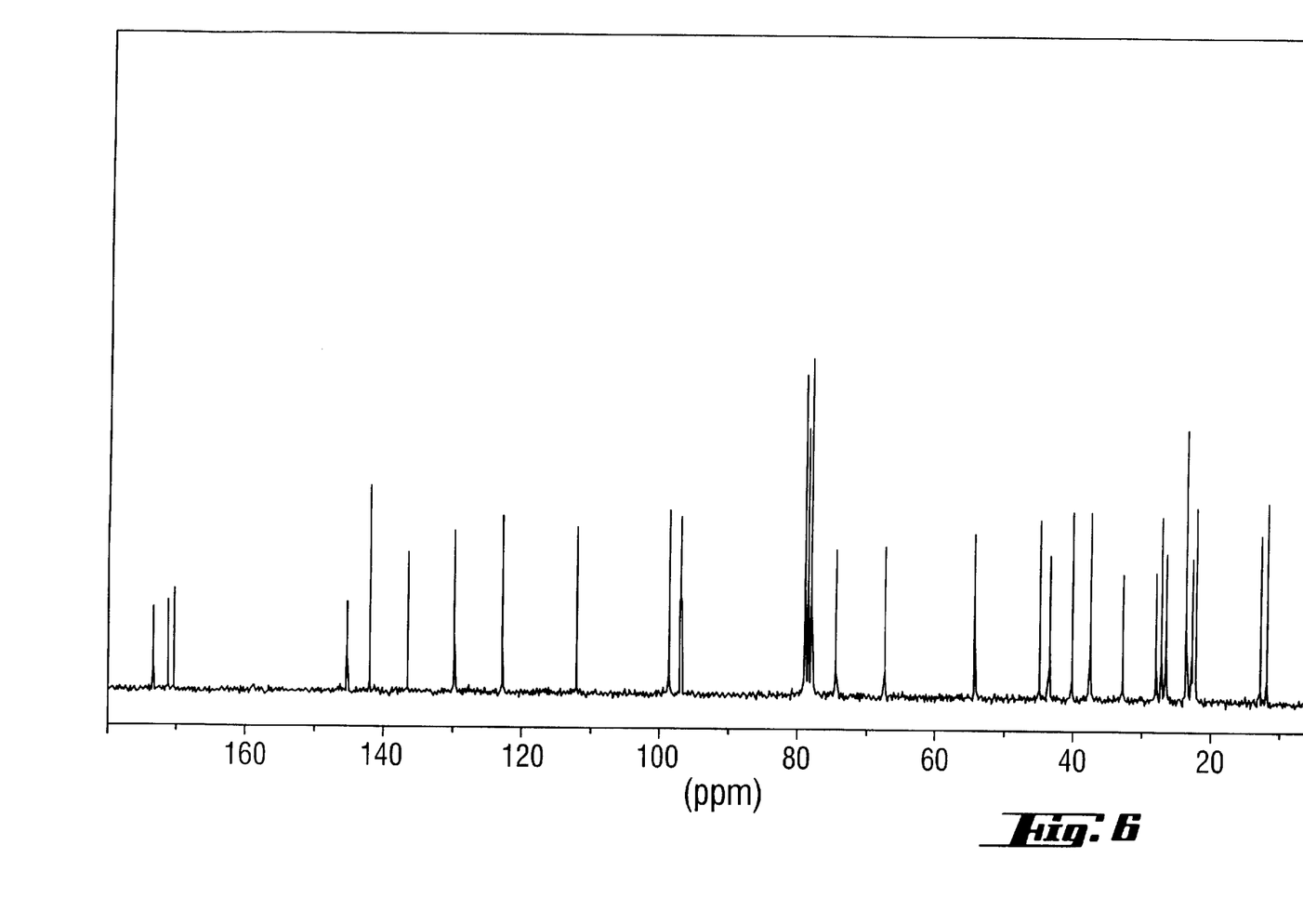
FIG. 6 illustrates the $^{13}$C NMR (75 MHz,CDCl$_3$) of Esculentin B.

|  | Esculentin A | Esculentin B |
| --- | --- | --- |
| Nature | White solid | White solid |
| Solubility | $CH_2Cl_2$, $CHCl_3$, EtOAc, MeOH, $CH_3CN$ and DMSO | $CH_2Cl_2$, $CHCl_3$, EtOAc, MeOH, $CH_3CN$ and DMSO |
| Melting point | 176–178° C. | 145–147° C. |
| $[\alpha]_D$ | −137.67° (c 0.32, $CHCl_3$) | +56.15° (c 0.32, $CHCl_3$) |
| HPLC RT | 18.2 min | 16.9 min |
|  | [Column: 4 mm × 250 mm EUROSPHERE 100-C18 (5μ); Mobile phase: 50% $CH_3CN$ in water to 100% $CH_3CN$ in 25 min.; Flow rate: 1 ml/min.; Detection: 220 nm] | |
| Elemental analysis: |  |  |
| Calcd. for | $C_{24}H_{32}O_6$ | $C_{29}H_{42}O_9$ |
|  | C 69.23; H 7.69 | C 65.16; H 7.86 |
| Found | C 69.96; H 7.61 | C 65.71; H 7.79 |
| EI-MS (Electron Impact Mass Spectrum) | 356 (M-ACOH)$^+$ | 474 (M-AcOH)$^+$ |
| Molecular weight | 416 | 534 |
| Molecular formula | $C_{24}H_{32}O_6$ | $C_{29}H_{42}O_9$ |
| UV (MeOH) | 224 nm | 232 nm |
| IR (KBr) | FIG. 1 of the accompanying drawings | FIG. 4 of the accompanying drawings |
| $^1$H NMR (300 Mhz, $CDCl_3$) | FIG. 2 of the accompanying drawings | FIG. 5 of the accompanying drawings |
| $^{13}$C NMR (75 Mhz, $CDCl_3$) | FIG. 3 of the accompanying drawings | FIG. 6 of the accompanying drawings |

Esculentin A and Esculentin B showed interesting activity against LPS-stimulated release of IL-1α and TNF-α in human mononuclear cells. Further, both the compounds were found to possess cytotoxicity against He La and Vero cell lines and may, therefore, be useful also as anticancer agents.

The foregoing written description relates to various embodiments of the present invention. Numerous changes and modifications may be made therein without departing from the spirit and scope of the invention as defined in the following claims.

What is claimed is:

1. An isolated compound of the formula 1

Esculentin A (1)

or a pharmaceutically acceptable derivative thereof.

2. An isolated compound of the formula 2

Esculentin B (2)

or a pharmaceutically acceptable derivative thereof.

3. A process for the isolation of one or both of the compounds 18β, 19β-diacetyloxy-18α, 19α-epoxy-3, 13(16), 14-clerodatrien-2-one (Esculentin A) and 18β, 19β-diacetyloxy-18α, 19α-epoxy, 12, 14-clerodatrien-2β-isovaleryloxy-6β, 7α-diol (Esculentin B) from plant material of a plant belonging to the Samydaceae family, comprising extracting the plant material with an organic solvent in the ratio 1:2 to 10 parts by weight of the plant material to the organic solvent at a pH 5–8 and recovering the compound or compounds from the solvent extract.

4. A process as claimed in claim 3 further comprising converting the compound or compounds into pharmaceutically acceptable derivative or derivatives thereof.

5. A process as claimed in claim 3 wherein the plant belonging to the Samydaceae family is *Casearia esculenta*.

6. A process as claimed in claim 3, wherein the plant material comprises twigs.

7. A process as claimed in claim 3, wherein the extraction is carried out with petroleum ether followed by dichloromethane.

8. A process as claimed in claim 3, wherein the extraction is carried out in the ratio 1:5 parts by weight of the plant material to the organic solvent.

9. A process as claimed in claim 3, wherein the extraction is carried out at pH 7.

10. A pharmaceutical composition comprising an effective amount of the compound of the formula 2 as claimed in claim 2 and a pharmacologically tolerated carrier.

11. A pharmaceutical composition comprising an effective amount of the compound of the formula 1 as claimed in claim 1, and a pharmacologically tolerated carrier.

12. An anti-inflammatory agent comprising a compound of the formula 2 as claimed in claim 2.

13. An anti-inflammatory agent comprising a compound of the formula 1 as claimed in claim 1.

14. An anti-arthritic agent comprising a compound of the formula 2 as claimed in claim 2.

15. An anti-arthritic agent comprising a compound of the formula 1 as claimed in claim 1.

16. A method for the manufacture of a medicament for the treatment of cancer, which comprises incorporating into said medicament a compound of the formula 2 as claimed in claim 2.

17. A method for the manufacture of a medicament for the treatment of cancer, which comprises incorporating into said medicament a compound of the formula 1 as claimed in claim 1.

18. A method for the treatment of cancer which comprises administering an effective amount of the compound of the formula 2 as claimed in claim 2.

19. A method for the treatment of cancer which comprises administering an effective amount of the compound of the formula 1 as claimed in claim 1.

* * * * *